United States Patent [19]

Le Fur et al.

[11] 4,435,410

[45] Mar. 6, 1984

[54] 3-[2-(3-ALKYL AND ALKENYL-4-PIPERIDYL)-ETHYL]-INDOLES FOR INHIBITING SEROTONIN UPTAKE AND FOR RELEASING SEROTONIN

[75] Inventors: Gerard R. Le Fur, Plessis Robinson; Christian L. A. Renault, Taverny, both of France

[73] Assignee: Pharmindustrie, Gennevilliers, France

[21] Appl. No.: 374,366

[22] Filed: May 3, 1982

[30] Foreign Application Priority Data

May 22, 1981 [FR] France ................ 81 10219

[51] Int. Cl.³ .................. A61K 31/445; C07D 401/06
[52] U.S. Cl. ..................... 424/267; 546/201; 546/226; 546/248
[58] Field of Search ........... 546/201; 424/267

[56] References Cited

U.S. PATENT DOCUMENTS 4,064,255 12/1977 Champseix et al. ............ 424/267

FOREIGN PATENT DOCUMENTS

| 7258 | 1/1980 | European Pat. Off. | 546/201 |
| 1289690 | 2/1962 | France | 546/201 |
| M1693 | 2/1963 | France | 546/201 |
| 1510003 | 12/1967 | France | 546/201 |
| M6291 | 9/1968 | France | 546/201 |
| 925429 | 5/1963 | United Kingdom | 546/201 |
| 1023781 | 3/1966 | United Kingdom | 546/201 |

OTHER PUBLICATIONS

Gray, A., et al., J. Org. Chem., 26, 3368 (1961).
Chemical Abstracts, 90:168582y (1979) [Belgian 862,346, Loevens, 6/27/78].

Primary Examiner—Richard A. Schwartz
Attorney, Agent, or Firm—Beveridge, DeGrandi & Kline

[57] ABSTRACT

Compounds of the general formula:

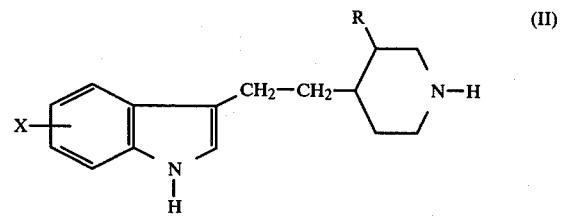

in which X represents a hydrogen or halogen atom, for example fluorine or chlorine, and R represents an alkyl group having 1 to 3 carbon atoms or alkenyl group having 2 to 3 carbon atoms are disclosed together with methods for their preparation and their use in the treatment of migraines, as anti-thrombosis agents or as rapid acting thymoanaleptic medicaments.

7 Claims, No Drawings

3-[2-(3-ALKYL AND ALKENYL-4-PIPERIDYL)-ETHYL]-INDOLES FOR INHIBITING SEROTONIN UPTAKE AND FOR RELEASING SEROTONIN

The present invention relates to new indole derivatives and their use as medicaments.

French Patent No. 75,38051 (No. 2,334,358) which corresponds to U.S. Pat. No. 4,064,255, was filed on Dec. 12, 1975 and describes indole derivatives which are active as specific inhibitors of the uptake of serotonin by the neurons and which can, as a result of this, find uses a psychotropic medicaments, particularly as anti-depressants. As such, special reference may be made to 3-[2-(4-piperidyl)-ethyl]-indole of the formula:

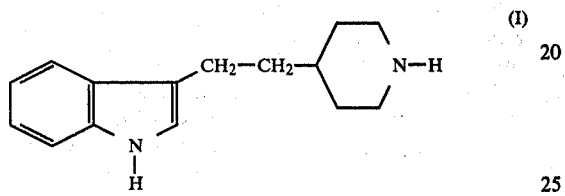

or indalpine, G. Le Fur and coll. Life Sciences 23, 1959 (1978).

With respect to new products, the object of the present invention is compounds of the general formula:

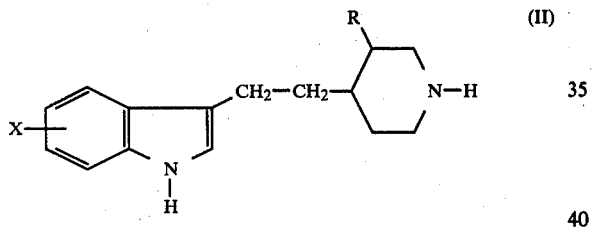

in which X represents an atom of hydrogen or of halogen, for example fluorine or chlorine, and R represents an alkyl which contans 1 to 3 carbon atoms or an alkenyl group which contains 2 to 3 carbon atoms.

It has in fact been found, in accordance with the present invention, that the compounds of formula (II) possess not only the property like indalpine of inhibiting the uptake of serotonin, but also the property of causing the release of serotonin which is contained either in the neurons or in the blood platelets. This double function reveals itself in a more intense and more rapid action on depression as a result of the neuron release of serotonin in the synaptic cleft, together with inhibition of the uptake. The release of serotonin from the platelets into the blood plasma improves migraine conditions; finally, depletion of the platelets in serotonin prevents arterial thrombi from forming.

The molecule of the compound of formula (II) contains two asymmetrical atoms of carbon; consequently, for a given significance of X and R, there are two diastereoisomers which are called the cis compound and the trans compound respectively, depending on whether the R group and the group fixed in the 4 position on the piperidyl cycle are in a cis position or a trans position in relation to one another. These two diastereoisomers may be represented schematically by the following formulae:

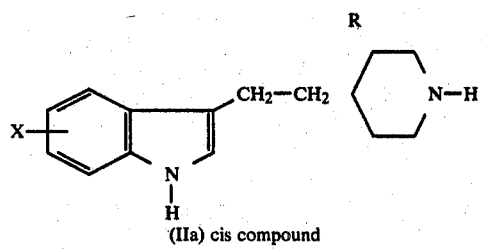
(IIa) cis compound

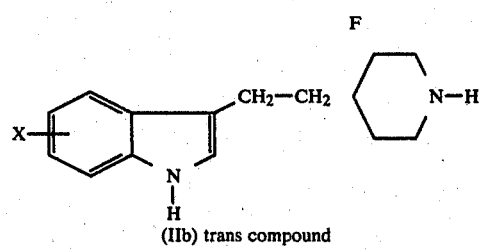
(IIb) trans compound

Each diastereoisomer has corresponding to it one racemic and two enantiomers, each enantiomer corresponding to a specific absolute configuration, which is either rectus (R) or sinister (S), of the carbons in the 3 and 4 positions of the piperidyl ring.

The various isomers referred to above and mixtures of the same form part of the present invention.

Compounds of general formula (II) can be prepared by reaction of an indole derivative of the formula:

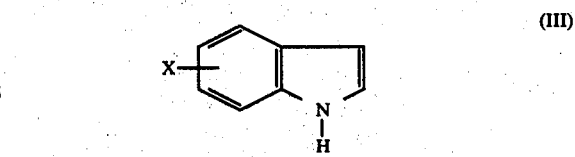

in which X has the same significances as in formula (II), with a metallic derivative of the formula R'Li in which R' represents an alkyl group having 1 to 4 carbon atoms, e.g., methyllithium, or butyllithium, an aryl group having 6 carbon atoms, e.g., phenyllithium, or a dialkylamino group wherein the alkyl group has from 1 to 6 carbon atoms, reaction of the metallized compound thus obtained (formula IV in the diagram below) with a piperidine derivative of the formula:

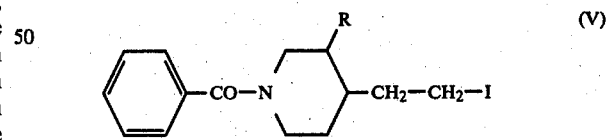

in which R has the same significances as in formula (II), and hydrolysis of the compound thus obtained (formula VI). The whole of the reactions can be expressed schematically as follows:

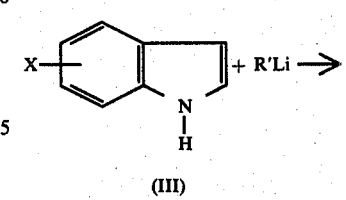

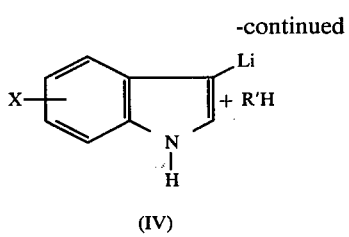

(IV)

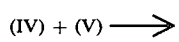

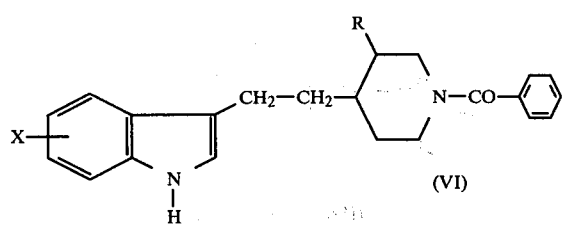

(VI)

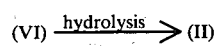

The reaction designated (a) above is effected in an inert solvent therefor, e.g., an ether such as diethyl oxide, tetrahydrofuran or dimethoxyethane or a hydrocarbon such as benzene, toluene or xylene or a mixture of these solvents, at a temperature of between −10° and +20° C. As an R' Li metallic derivative, preferably phenyllithium, butyllithium or lithium diisopropylamide are used.

The condensation reaction (b) is effected in the same solvents as reaction (a) and at a temperature of between a 0° C. and the boiling point of the solvent.

The hydrolysis reaction (c) which consists of replacing the benzoyl group by an atom of hydrogen is effected according to known methods, for example, by means of sodium hydroxide in a hydro-organic medium such as a mixture of water and ethyleneglycol or a mixture of water and the monomethyl ether of ethyleneglycol, at the boiling point of the medium used.

The piperidine derivatives of formula (V) can be prepared according to the following reaction scheme:

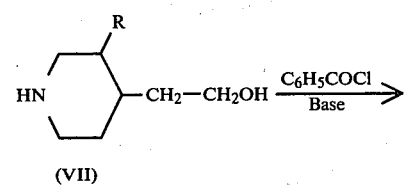

(VII)

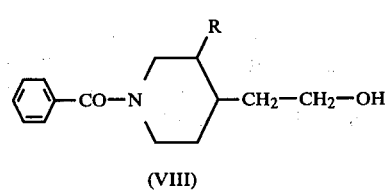

(VIII)

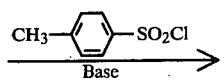

(VIII)

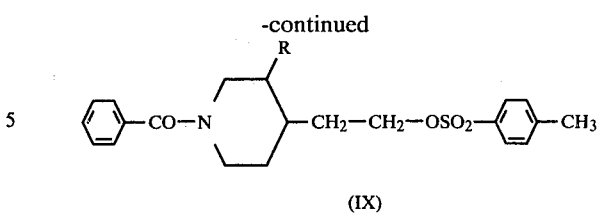

(IX)

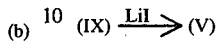

Reaction (d) of benzoyl chloride on the alcohols of formula (VII) is advantageously effected in the presence of an organic base such as a tertiary amine, for example triethylamine, or an inorganic base such as sodium or potassium hydroxide or carbonate in an aqueous solution. The operation is carried out in an inert solvent such as chloroform or 1,1,1-trichloroethane at a temperature of between 20° C. and the boiling point of the solvent used.

The reaction (e) of paratoluene sulfonyl chloride (tosyl chloride) with the alcohols of formula (VIII) is effected at a temperature of between −20° C. and the ambient temperature in an inert solvent such as chloroform or toluene. and in the presence of a base, preferably an amine such as trichlylamine or pyridine. An advantageous method consists of operating in pyridine which acts, at one and the same time, as solvent and base.

The products obtained of formula (IX) are then treated (reaction f) with lithium iodide in an inert solvent such as acetone or methylethylketone at a temperature between 0° C. and 30° C.

Products of formula (II) may also be prepared by reduction of ketone derivatives of the general formula:

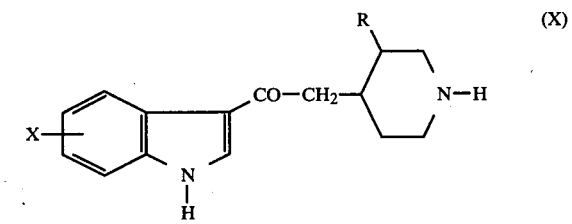

in which R and X have the same significance as in formula (II).

As a reducing agent there can be used a metallic hydride such as sodium, potassium or lithium borohydride, or lithium triethylborohydride or aluminium and lithium hydride in suitable solvents which are known for each of these reducing agents, at temperatures of between 0° C. and the boiling point of the solvent used.

The ketone derivatives of formula (X) may be prepared according to the following reaction scheme:

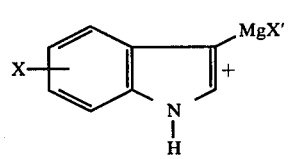

(XI)

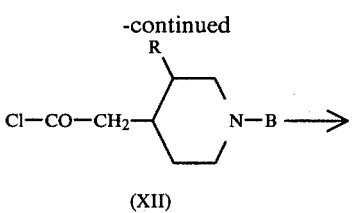

(XII)

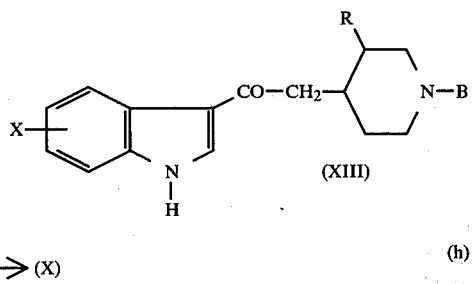

(XIII) $\xrightarrow{\text{acid}}$ (X)  (h)

The Grignard reagent of formula (XI) in which X has the same significance as in formula (II) and X' represents an atom of chlorine, of bromine or of iodine, is obtained by the action on the corresponding indole of a magnesium alkyl halide such as magnesium methyl chloride, bromide or iodide in an ether such as diethyl ether, generally at the boiling point of the solvent. To the solution obtained in this way and cooled to a temperature of between −10° C. and +20° C., there is added (reaction g) the acid chloride of formula (XII) in which B represents the benzyloxycarbonyl group and R has the same significance as in formula (II). In this way, compounds of formula (XIII) are obtained. Fission of the benzyloxycarbonyl group (reaction h) may be effected by a acid such as hydrochloric acid in an inert solvent such as acetic acid or ethanol at a temperature of between 20° C. and the boiling point of the solvent used.

The acid chlorides of formula (XII) may be prepared in two stages starting from 4-piperidyl acetic acids of formula XIV below in which R has the same significance as in formula (II) in accordance with the following reaction scheme:

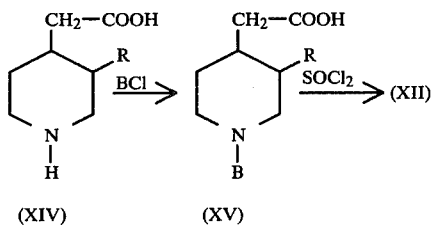

The acids of formula (XIV) are treated with benzyl chloroformate (BCl) in solution in a hydrocarbon in the presence of a base such as sodium hydroxide in an aqueous solution at a temperature of between 10° and 40° C. The acids obtained of formula (XV) are converted into acid chlorides of formula (XII) by the action of a chlorinating agent such as thionyl chloride in an inert solvent such as chloroform and at the boiling point of the solvent used.

Compounds of formula (II) in which R represents an alkyl group possessing 2 to 3 carbon atoms may also be prepared by catalytic hydrogenation of the corresponding products of formula (II) in which R represents an alkenyl group, or of their salts. This hydrogenation may be effected at atmospheric pressure, at a temperature of between 20° and 50° C. in an inert solvent such as an alcohol (for example, methanol or ethanol) or an acid (for example, acetic acid) in the presence of a catalyst such as palladium, nickel, rhodium, ruthenium or platinum.

Compounds of formula (II) in which R represents the vinyl group and in which the carbon atoms of the piperidine ring which carries the vinyl group has a given rectus (R) or sinister (S) configuration, can be prepared by heating, at a temperature in excess of 50° C. in a protic solvent (such as water, methanol or ethanol, or a mixture of said protic solvents, in the presence or absence of formaldehyde, the corresponding compounds of formula (II) in which R represents the vinyl group and in which the carbon atom of the piperidine ring which carries the vinyl group has the reverse configuration—sinister (S) or rectus (R), partly or totally salified, according to the process of European Pat. No. 0,005,654 which corresponds to U.S. Pat. No. 4,238,612. Heating may be effected in particular in an acid aqueous medium with a pH in the region of 6, at a temperature of between 120° and 160° C.

The reaction mixtures obtained according to various processes described above are treated by chemical methods which are either physical (evaporation, extraction with a solvent, distillation, crystallization, chromotagraphy, etc.) or chemical (formation of salt and regeneration of the base, etc.) in order to isolate the compounds of formula (II) in the pure state.

Compounds of formula (II) in the form of free bases may if desired, be converted into addition salts with a pharmaceutically acceptable mineral or organic acid, e.g. hydrochloric acid, sulfuric acid, acetic acid or maleic acid, by the action of such an acid in a suitable solvent, e.g. ethanol, acetone or ethyl acetate.

The following examples illustrate the invention without limiting it. The data relating to the nuclear magnetic resonance spectra (hereinafter N.M.R.) which appear in these examples relate to the nuclear magnetic resonance of the protons of the compounds in the base state in solution in deuterochloroform (unless otherwise stated). The chemical displacements δ are measured using tetramethylsilane as reference.

EXAMPLE 1

3-[2-(3(R)VINYL-4(R)PIPERIDYL)-ETHYL]-INDOLE 52 ml of a 1.6 M solution of butyllithium in hexane were introduced at 0° C. into 10 g of indole in 150 ml of toluene under nitrogen. Then 15 g of 1-benzoyl-3(R)vinyl-4(S)iodoethylpiperidine in solution in 50 ml of toluene were added and the reaction mixture was held at 50° C. for 20 hours. The organic mixture was poured onto 2 N hydrochloric acid, the insoluble substance extracted with methylene chloride, and the organic solution washed with water, dried over magnesium sulfate and evaporated to dryness under reduced pressure. 21 g of product were obtained and this was subjected to chromatography over silica by means of an 80–20 toluene-diethylamine mixture as eluant. 5.3 g of product were recovered and treated for 9 hours with 50 ml of an aqueous solution of 3 N sodium hydroxide and 50 ml of the monomethyl ether of ethyleneglycol. The solvents were evaporated under reduced pressure, the residue partitioned between water and chloroform, and the organic phase washed with water, dried and evaporated to dryness. 2.7 g of product were recovered and recrystallized in absolute ethanol to give 2 g of 3-[2-(3(R)vinyl-4(R)piperidyl)-ethyl]-indole which melted at 168° C.

The 1-benzoyl-3(R)vinyl-4(S)iodoethyl-piperidine was prepared in 3 stages as follows:

1-BENZOYL-3(R)VINYL-4(S)PIPERIDYL-ETHANOL

A mixture of 20 g of 3(R)vinyl-4(S)piperidyl-ethanol, 19.7 g of benzoyl chloride and 108 g of potassium carbonate in 250 ml of chloroform and 11 ml of water were kept for 2 hours under reflux.

After cooling, the reaction mixture was filtered and the filtrate evaporated under reduced pressure. The residue was chromatographed over silica gel by means of a mixture of cyclohexane and ethyl acetate (7:3) as the eluant. In this way, 24 g of 1-benzoyl-3(R)vinyl-4(S)piperidyl-ethanol were obtained in the form of an oil.

N.M.R. spectrum of the product obtained:
$C_6H_5$ δ: 7.4 p.p.m.
$CH_2$=CH— δ: 5 p.p.m.
$CH_2$=CH— δ: 6 p.p.m.
—$CH_2$—OH δ: 3.6 p.p.m.

The 3(R)vinyl-4(S)piperidyl-ethanol may be prepared in accordance with R. Lukes, Chem. Listy, 47, 858 (1953).

1-BENZOYL-3(R)VINYL-4(S)-[(4-METHYL-PHENYL)SULFONYLOXYETHYL]PIPERIDINE 80 g of 1-benzoyl-3(R)vinyl-4(S)piperidyl-ethanol and 73 g of p.-toluenesulfonyl chloride in 1 liter of pyridine were stirred at −10° C. for 2 hours. The reaction mixture was poured into 3 liters of water and the insoluble substance extracted with 2 liters of ether. The organic phase was washed 4 times with 1 liter each time of 0.1 N hydrochloric acid and 5 times with 1 liter each time of water; it was dried over anhydrous magnesium sulfate, filtered and evaporated to dryness under reduced pressure. In this way, 66 g of 1-benzoyl-3(R)vinyl-4(S)-[(4-methyl-phenyl)sulfonyloxyethyl]-piperidine were obtained in the form of an oil.

N.M.R. spectrum of the product obtained:

$C_6H_5$ δ: 7.4 p.p.m.

—$CH_2$—O—$SO_2$— δ: 4 p.p.m.

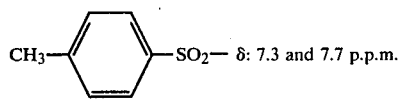 δ: 7.3 and 7.7 p.p.m.

 δ 2.4 p.p.m.

1-BENZOYL-3(R)VINYL-4(S)IODOETHYL-PIPERIDINE 24.7 g of 1-benzoyl-3(R)vinyl-4(S)-[(4-methyl-phenyl)sulfonyloxyethyl]-piperidine and 16.4 g of lithium iodide were agitated for 24 hours at ambient temperature in 220 ml of acetone. The reaction mixture was filtered, the solvent evaporated under reduced pressure and the residue dissolved again in ethyl acetate.

The organic phase was washed with water, dried over magnesium sulfate and evaporated to dryness under reduced pressure. In this way, 16 g of 1-benzoyl-3(R)vinyl-4(S)iodoethyl-piperidine were obtained in the form of an oil.

N.M.R. spectrum of the product obtained:
$C_6H_5$ δ: 7.4 p.p.m.
$CH_2$=CH— δ: 5 p.p.m.
$CH_2$=CH— δ: 6 p.p.m.
—$CH_2$—I δ: 3.2 p.p.m.

EXAMPLE 2

3-{2-[3(R)ETHYL-4(R)PIPERIDYL]-ETHYL}-INDOLE 250 ml of a molar solution of lithium triethylborohydride in tetrahydrofuran were added to 17 g of 2-[3(R)ethyl-4(S)piperidyl]-1-(3-indolyl)-ethanone in 250 ml of anhydrous tetrahydrofuran under nitrogen, at ambient temperature. The reaction mixture was kept for 18 hours under reflux and then cooled to 0° C. 300 ml of water and 400 ml of ethyl ether were added and the organic phase was recovered, washed with water, dried over magnesium sulfate and evaporated to dryness under reduced pressure. 7 g of product were obtained and chromatographed over silica gel by means of a mixture of methanol-acetone-diethylamine (5-5-0.5) as eluant. After crystallization in isopropyl ether, 3.7 g of 3-{2-[3(R)ethyl-4(R)piperidyl]-ethyl}-indole which melted at 150° C. were obtained.

The 2-[3(R)ethyl-4(S)piperidyl]-1-(3-indoly)-ethanone was prepared as follows:

A solution of 2.3 g of indole in 15 ml of ethyl ether was added under nitrogen to 14 ml of a 3 M solution of magnesium methyl iodide in ether. The reaction mixture was taken over one hour to reflux and then cooled to 0° C. At this temperature, 15 ml of a 1.3 molar solution of 1-benzyloxycarbonyl-3(R)ethyl-4(S)-piperidine acetic acid chloride in ethyl ether was added. Agitation took place for 24 hours at ambient temperature; it was then cooled to 0° C. and 60 ml of ethyl ether and 60 ml of 2 N hydrochloric acid were added. The organic phase was recovered, washed with water, dried and evaporated to dryness under reduced pressure. 7 g of oil were obtained and treated with 150 ml of 10 N hydrochloric ethanol for 2 hours under reflux. The solvent was evaporated and the residue was chromatographed over silica gel with a mixture of methanol-acetone-diethylamine (5-5-0.5) as eluant. In this way, 2 g of 2-[3(R)ethyl-4(S)piperidyl]-1-(3-indolyl)-ethanone were obtained in the form of an oil.

N.M.R. spectrum of the product obtained:

$CH_3$—$CH_2$— δ: 0.9 p.p.m.

$$-\underset{\underset{O}{\|}}{C}-CH_2- \text{ and}$$

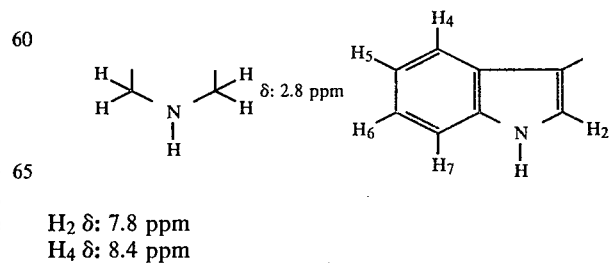

$H_2$ δ: 7.8 ppm
$H_4$ δ: 8.4 ppm

H$_5$, H$_6$, H$_7$ δ: 7.2 ppm

The 1-benzyloxycarbonyl-3(R)-ethyl-4(S)piperidineacetic acid chloride was obtained as follows:

62 ml of a solution of 40% benzyl chloroformate in toluene were added at 10° C. to 31 g of 3(R)ethyl-4(S)piperidineacetic acid hydrochloride (cincholoipon) in 170 ml of water and 42 ml of an aqueous solution of 10 N sodium hydroxide. Agitation took place for 20 hours at ambient temperature and the organic phase was washed 2 times with 250 ml each time of ethyl ether. The aqueous phase was acidified with concentrated hydrochloric acid and extracted 2 times with 250 ml each time of chloroform. The organic phase was dried over anhydrous magnesium sulfate and evaporated to dryness under reduced pressure. 45 g of oil were obtained and treated directly in 500 ml of chloroform with 22 ml of thionyl chloride for 2 hours under reflux. The solvent was eliminated under reduced pressure and 48 g of 3(R)ethyl-4(S)-piperidine-acetic acid chloride were recovered and used in the form of a 1.3 molar solution in ethyl ether.

EXAMPLE 3

3-{[3(R)ETHYL-4(R)PIPERIDYL]-ETHYL}-INDOLE 0.250 g of 3-{[3-(R)vinyl-4(R)piperidyl]-ethyl}-indole in 1 ml of normal hydrochloric acid and 9 ml of methanol in the presence of 0.04 g of platinum oxide as catalyst were hydrogenated for 3 hours at ambient temperature and at atmospheric pressure. The catalyst was filtered, the filtrate evaporated to dryness, the residue made up in 100 ml of water, the aqueous phase washed with ether and alkalinized with an aqueous solution of sodium hydroxide and the insoluble substance was extracted with ethyl acetate. The organic phase was dried over magnesium sulfate and evaporated to dryness under reduced pressure. 0.180 g of product which melted at 150° C. was obtained.

EXAMPLE 4

3-{2-[3(S)VINYL-4(R)PIPERIDYL]-ETHYL}-INDOLE

A solution of 1.36 g of 3-[2-(3-(R)vinyl-4(R)piperidyl)-ethyl]-indole in 210 ml of water and 5.3 ml of N hydrochloric acid was kept at 160° C. for 48 hours. After cooling, the solution was alkalinized by means of potassium carbonate and extracted with ethyl acetate. The organic phase was dried over magnesium sulfate and evaporated to dryness under reduced pressure; 1.2 g of product were obtained and chromatographed over silica by means of a 95-5 mixture of toluene and diethylamine as eluant. 0.45 g of product were obtained and recrystallized in absolute ethanol to give 0.17 g of 3-{2-[3(S)vinyl-4(R)piperidyl]-ethyl}-indole which melted at 168° C.

PHARMACOLOGICAL PROPERTIES

It is known that the uptake of serotonin by the blood platelets constitutes a good model for the uptake of this amine by the neurons (cf. J. Tuomisto, J. Pharm. Pharmac., 26. 92 (1974). When it is applied to the study of medicaments, a method which makes use of the blood platelets is very attractive from the point of view of allowing human cells to be used, thereby giving it good prospects.

The ability of products to inhibit the uptake of serotonin or to cause its release has been shown on human blood platelets according to J. L. David and Coll. "Platelets Function and Thrombosis, a Review of Methods", p. 335 (Plenum Press, London, 1972).

(1) Inhibition of the uptake of serotonin

The results are expressed by a 50% inhibiting dose or I$_{50}$ which represents the dose of the product in micromoles per liter, reducing the uptake of serotonin by 50%.

(2) Release of serotonin

The action of the products on the release of serotonin is tested at a concentration of $5 \times 10^{-5}$ moles per liter. The results obtained are expressed as a percentage of increase in the release of serotonin as compared with the results obtained with controls.

The results obtained with the compounds according to the invention are shown in the table below. The table shows, for purposes of comparison, the results obtained two two reference products (imipramine and p-chloroamphetamine) and with indalpine.

TABLE

| Product | Inhibition of serotonin uptake I$_{50}$ (micromoles per liter) | Percent of increased serotonin release (product concentration: $5 \times 10^{-5}$ moles per liter) |
|---|---|---|
| Example 1 | 0.008 | 84 |
| Example 2 | 0.06 | 75 |
| Example 4 | 0.035 | 91 |
| Indalpine | 0.035 | 22 |
| Imipramine | 0.4 | 13 |
| p-chloro-amphetamine | 12 | 51 |

It can be seen from the table that the products of the invention are not only powerful inhibitors of the uptake of serotonin (activities equivalent to those of indalpine) but they are also powerful agents for the release of serotonin, being even more active than p-chloroamphetamine.

The interest of these compounds is found in the fact that, like p-chloroamphetamine, they induce release of serotonin without, however, having any of the other pharmacological properties characteristic of the amphetamine group (anorexia, hypermotility).

TOXICOLOGICAL PROPERTIES

The acute toxicity of the products was determined in male mice CD$_1$ (Charles RIVER) by oral administrations. The LD$_{50}$ which was calculated after 3 days' observation, by the cumulative method of J. J. Reed and Coll. (Am. J. Hyg. 27, 493-1938) is 225 mg/kg for the compound of Example 1, and about 200 mg/kg for the compound of Example 4.

The compounds according to the invention are atoxic at 100 mg/kg and, consequently, they behave as substances of relatively low toxicity in mice.

THERAPEUTIC APPLICATION

The compounds of the invention and their pharmaceutically acceptable salts may be used in human therapy in the form of tablets, capsules, gelatine coated pills, suppositories, ingestible or injectable solutions etc., as regulators of the serotonin-dependent vascular tonus, especially in the treatment of migraines, as anti-thrombosis agents and as thymoanaleptic medicaments with a particularly rapid action (on account of their action on the release of serotonin).

For the foregoing purposes the compounds described above may be administered in a therapeutically effective amount, such as to a mammal; orally or parenterally.

For purposes of injection the compounds described above can be prepared in the form of solutions, suspensions or emulsions in vehicles conventionally employed for this purpose.

The posology depends on the effects required and on the method of administration used. For example, by oral administration, it may be between 15 and 250 mg of active substance per day, with unit doses of between 5 and 50 mg.

Appropriate pharmaceutically acceptable carriers, diluents and adjuvants may be used together with the compounds described herein in order to prepare the desired compositions for use in treatment of mammals according to the invention.

The pharmaceutical compositions of this invention will contain the active compound together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide form for proper administration to the host.

What is claimed is:

1. A compound of the formula:

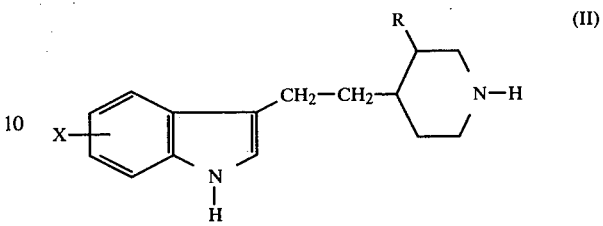

in which X represents hydrogen or halogen, and R represents alkyl having 1 to 3 carbon atoms or alkenyl having 2 to 3 carbon atoms.

2. The compound as claimed in claim 1 wherein said halogen is fluorine or chlorine.

3. The compound as claimed in claim 1 which has the cis structure, an enantiomer thereof or the racemate thereof.

4. The compound as claimed in claim 1 which has the trans structure, an enantiomer thereof or the racemate thereof.

5. A medicament useful as an agent for inhibiting the uptake of serotonin and for releasing serotonin which contains a pharmaceutically acceptable vehicle and as active substance 5 to 50 mg per unit dose of a compound according to claim 1 or its salt with a pharmaceutically acceptable acid.

6. A medicament as claimed in claim 5 for use in treatment of migraine, as an anti-thrombosis agent or as a thymoanaleptic agent 7. A method of treating a mammal afflicted with depression or migraine conditions or to prevent the formation of arterial thrombi, which comprises administering to said mammal a therapeutically effective amount of a composition containing a compound according to claim 1 or a pharmaceutically acceptable salt thereof in a pharmaceutically acceptable carrier therefor.

* * * * *